US012678310B2

(12) United States Patent
Krishnan et al.

(10) Patent No.: US 12,678,310 B2
(45) Date of Patent: Jul. 14, 2026

(54) SYSTEMS AND METHODS OF LOSSLESS TRANSMISSION AND REMOTE PRESENTATION OF RESPONSE FROM A CRANIAL SENSOR SYSTEM

(71) Applicant: Neurasignal, Inc., Los Angeles, CA (US)

(72) Inventors: Sivasankaran Krishnan, Bangalore (IN); Naveen Raghuveer, Andhra Pradesh (IN); Rahul Radhakrishnan, Alappuzha (IN); Jerine P. George, Ernakulam (IN); Yareeve Zemel, Studio City, CA (US); Karim Mohammed, Santa Clara, CA (US)

(73) Assignee: Neurasignal, Inc., Los Angeles, CA (US)

( * ) Notice: Subject to any disclaimer, the term of this patent is extended or adjusted under 35 U.S.C. 154(b) by 945 days.

(21) Appl. No.: 17/965,467

(22) Filed: Oct. 13, 2022

(65) Prior Publication Data

US 2023/0117404 A1 Apr. 20, 2023

Related U.S. Application Data

(60) Provisional application No. 63/255,911, filed on Oct. 14, 2021.

(51) Int. Cl.
*A61F 4/00* (2006.01)
*A61B 8/00* (2006.01)
*A61B 8/08* (2006.01)

(52) U.S. Cl.
CPC .............. *A61F 4/00* (2013.01); *A61B 8/0808* (2013.01); *A61B 8/488* (2013.01)

(58) Field of Classification Search
CPC ......... A61F 4/00; A61B 8/0808; A61B 8/488; A61B 8/4209; A61B 8/46; A61B 8/565
See application file for complete search history.

(56) References Cited

U.S. PATENT DOCUMENTS

| | | | | |
|---|---|---|---|---|
| 9,561,384 | B1 * | 2/2017 | Fischell | A61B 90/94 |
| 2015/0227702 | A1 * | 8/2015 | Krishna | A61B 5/7257 |
| | | | | 705/2 |
| 2016/0270679 | A1 * | 9/2016 | Mahon | A61B 5/388 |
| 2016/0287166 | A1 * | 10/2016 | Tran | A61B 5/74 |
| 2016/0323000 | A1 * | 11/2016 | Liu | H04W 4/80 |
| 2021/0038167 | A1 * | 2/2021 | Martineau | A61B 5/1121 |
| 2021/0137487 | A1 * | 5/2021 | Shi | A61B 8/485 |
| 2022/0181008 | A1 * | 6/2022 | Heldt | G16H 50/20 |
| 2022/0233860 | A1 * | 7/2022 | Hamner | A61N 1/36053 |
| 2023/0211157 | A1 * | 7/2023 | Badran | A61N 1/36034 |
| | | | | 607/48 |

* cited by examiner

*Primary Examiner* — Amine Benlagsir
(74) *Attorney, Agent, or Firm* — Polygon IP, LLP

(57) ABSTRACT

Example implementations include a system with a first communication channel operatively coupled with a cranial sensor system and operable to transmit a cranial sensor output obtained from the cranial sensor system to one or more remote devices, and a second communication channel operatively coupled with the cranial sensor system and operable to transmit a diagnostic output associated with the cranial sensor output to the remote device(s).

19 Claims, 16 Drawing Sheets

1600

700

210

212

Cloud System

Reader

Streaming API

Core API

Streaming API

Core API

Reader

Reader

1. GET organization/streaming/authorization

2. OK <token, streaming-api-end-point>

3. GET /streaming devices

4. Streaming devices list

5. Websocket connect <token>

6. Connect OK

7. Control Plane & TCD Data

1500

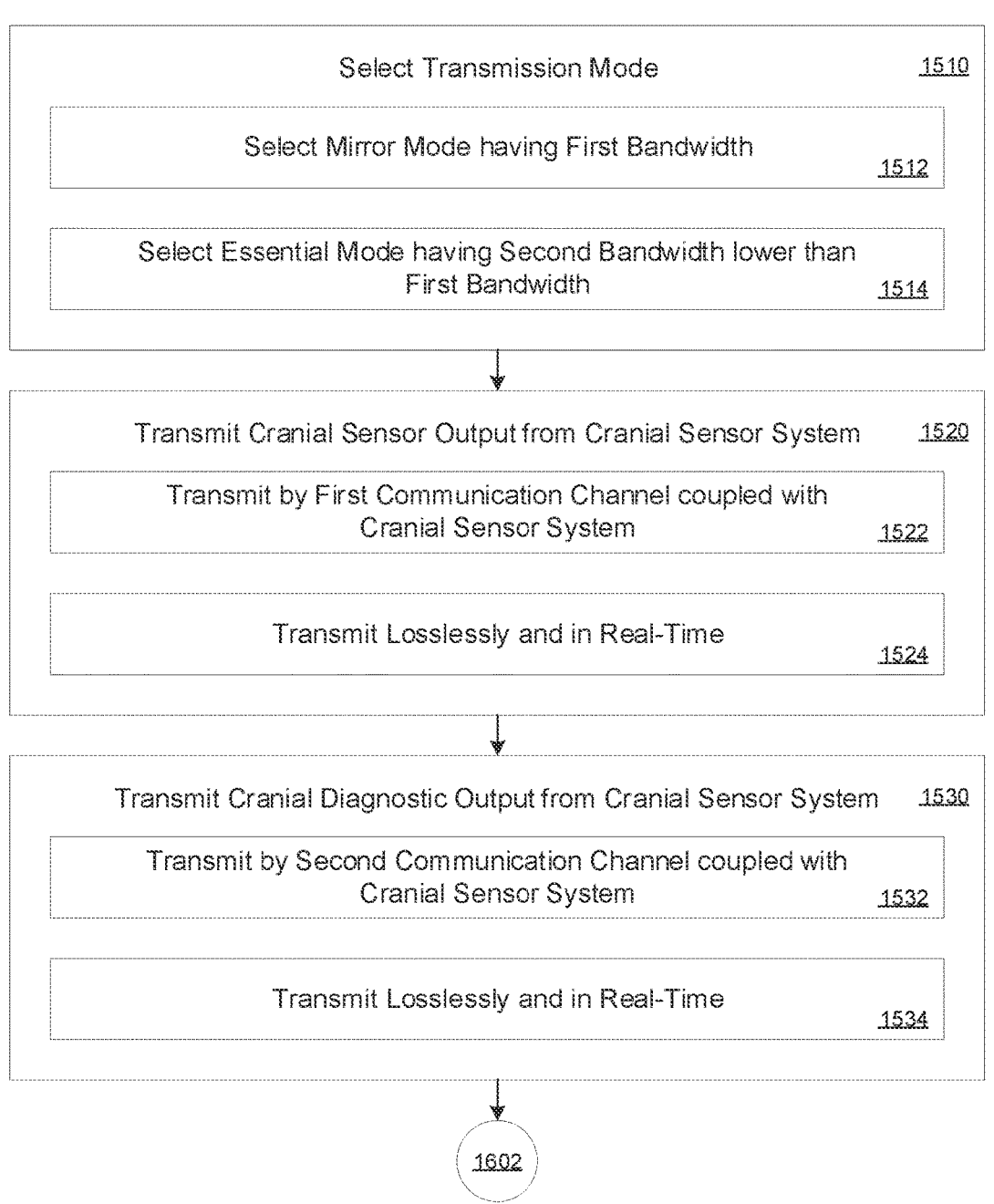

Select Transmission Mode                                    1510

Select Mirror Mode having First Bandwidth
                                                            1512

Select Essential Mode having Second Bandwidth lower than
First Bandwidth                                             1514

Transmit Cranial Sensor Output from Cranial Sensor System    1520

Transmit by First Communication Channel coupled with
Cranial Sensor System                                      1522

Transmit Losslessly and in Real-Time
                                                            1524

Transmit Cranial Diagnostic Output from Cranial Sensor System    1530

Transmit by Second Communication Channel coupled with
Cranial Sensor System                                      1532

Transmit Losslessly and in Real-Time
                                                            1534

SYSTEMS AND METHODS OF LOSSLESS TRANSMISSION AND REMOTE PRESENTATION OF RESPONSE FROM A CRANIAL SENSOR SYSTEM

CROSS-REFERENCE TO RELATED PATENT APPLICATION

This application claims priority from Provisional Application No. 63/255,911, filed Oct. 14, 2021, incorporated herein by reference in its entirety.

TECHNICAL FIELD

The present implementations relate generally to medical devices, and more particularly to lossless transmission and remote presentation of response from a cranial sensor system.

BACKGROUND

Transcranial Doppler ultrasound (TCD) is a noninvasive methodology for measuring Cerebral Blood Flow Velocity (CBFV) through the large arteries of the brain. The morphology of the pulsatile CBFV waveform can provide information concerning numerous cerebrovascular pathologies, including stroke, intracranial hypertension, and mild Traumatic Brain injury. TCD has proven effective for detecting occluded and stenosed cerebral arteries in the context of acute ischemic stroke. Additionally, CBFV waveforms acquired via TCD can provide evidence for cerebrovascular occlusion and stenosis. Thrombolysis in Brain Ischemia (TIBI) flow grades are widely used for this purpose but require subjective assessment by expert evaluators to be reliable. However, conventional systems cannot provide accurate and timely transmission of TCD or related signals to healthcare professionals, who may be located remotely. Without accurate and timely transmission of TCD or related signals to the appropriate healthcare professionals, response time and accurate assessment of patient condition can be delayed or prevented, significantly impacting patient health outcomes.

SUMMARY

Present implementations are directed to a system capable of losslessly transmitting output signals generated by a cranial sensor system to one or more remote locations. Thus, present implementations can enable medical personnel, including medical professionals, medical practitioners, caregivers, and the like, to receive accurate output from cranial sensor systems at any location. Because cranial monitoring by TCD, for example, must in many cases be conducted at a clinical site having specialized equipment, the sensor output of the cranial sensor system co-located with the equipment and the clinical site must be transmitted to the medical personnel if those medical personnel are not located at the clinical site or not located near the patient. Present implementations thus allow medical personnel to receive a response from a cranial sensor system while away from the clinical site, and allow, for example, the patient's physician to be connected to the patient continuously, and up to 24 hours a day and seven days a week. Thus, the physician can respond more immediately to anomalies in the response from the cranial sensor system at the clinical site, even without being physically present at the clinical site. A remote application that can take the form of, for example, a web application that can be executable from a remote device, including, for example, a smartphone, tablet, personal computer, computer, a television, a smart television, a smart watch, a connected smart watch, any web enabled or connected device, or the like, by one or more secure communication channels. In some implementations, a remote device includes but is not limited to a smartphone, mobile device, wearable mobile device, tablet computer, desktop computer, laptop computer, cloud server, local server, and the like. As one example, a physician can be in a different room in the same hospital and view output of the cranial sensor system even when the physician is not in the same room as the patient and the cranial sensor system. Authorized medical personnel can thus obtain and consume the response from the cranial sensor system anywhere and at any time.

Example implementations include a system with a first communication channel operatively coupled with a cranial sensor system and operable to transmit a cranial sensor output obtained from the cranial sensor system to one or more remote devices, and a second communication channel operatively coupled with the cranial sensor system and operable to transmit a diagnostic output associated with the cranial sensor output to the remote device.

BRIEF DESCRIPTION OF THE DRAWINGS

These and other aspects and features of the present implementations will become apparent to those ordinarily skilled in the art upon review of the following description of specific implementations in conjunction with the accompanying figures, wherein.

US 12,678,310 B2

3

Figure 12:
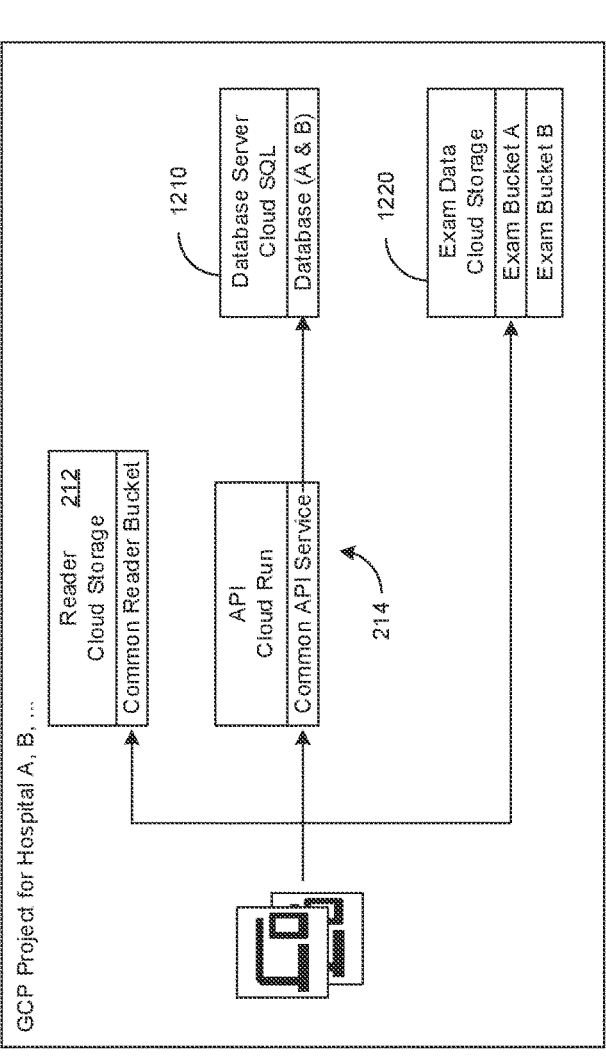

FIG. 12 illustrates a third example hospital site system for a cranial sensor system, in accordance with present implementations.

Figure 13:
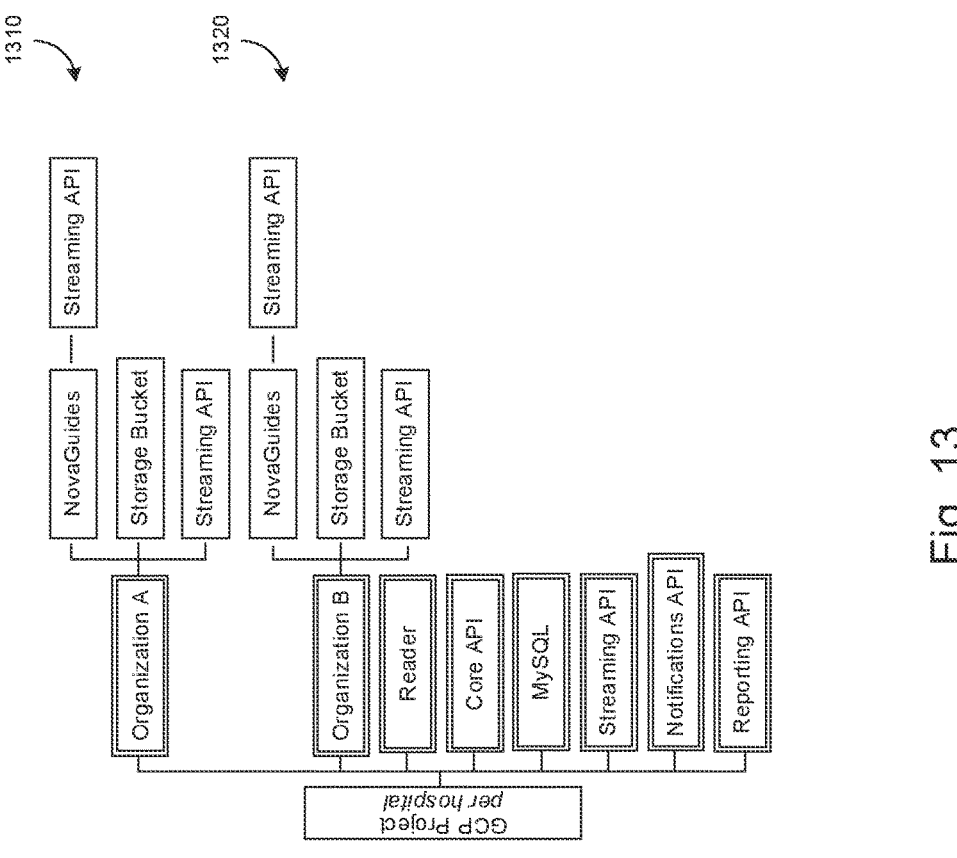

FIG. 13 illustrates a first streaming architecture for a cranial sensor system, in accordance with present implementations.

Figure 14:
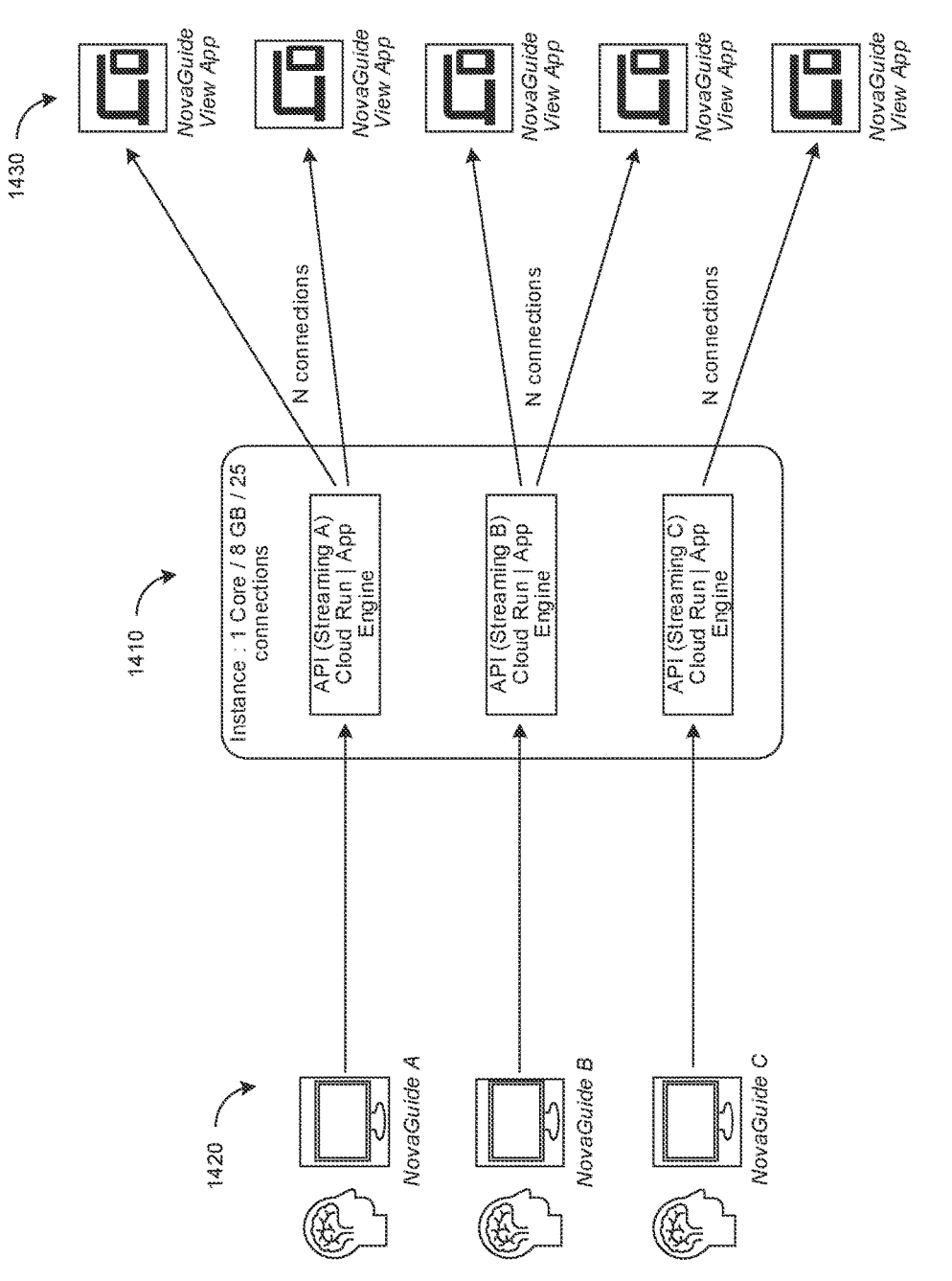

FIG. 14 illustrates a second streaming architecture for a cranial sensor system, in accordance with present implementations.

FIG. 15 illustrates an example method of transmission by a cranial sensor system, in accordance with present implementations.

Figure 16:
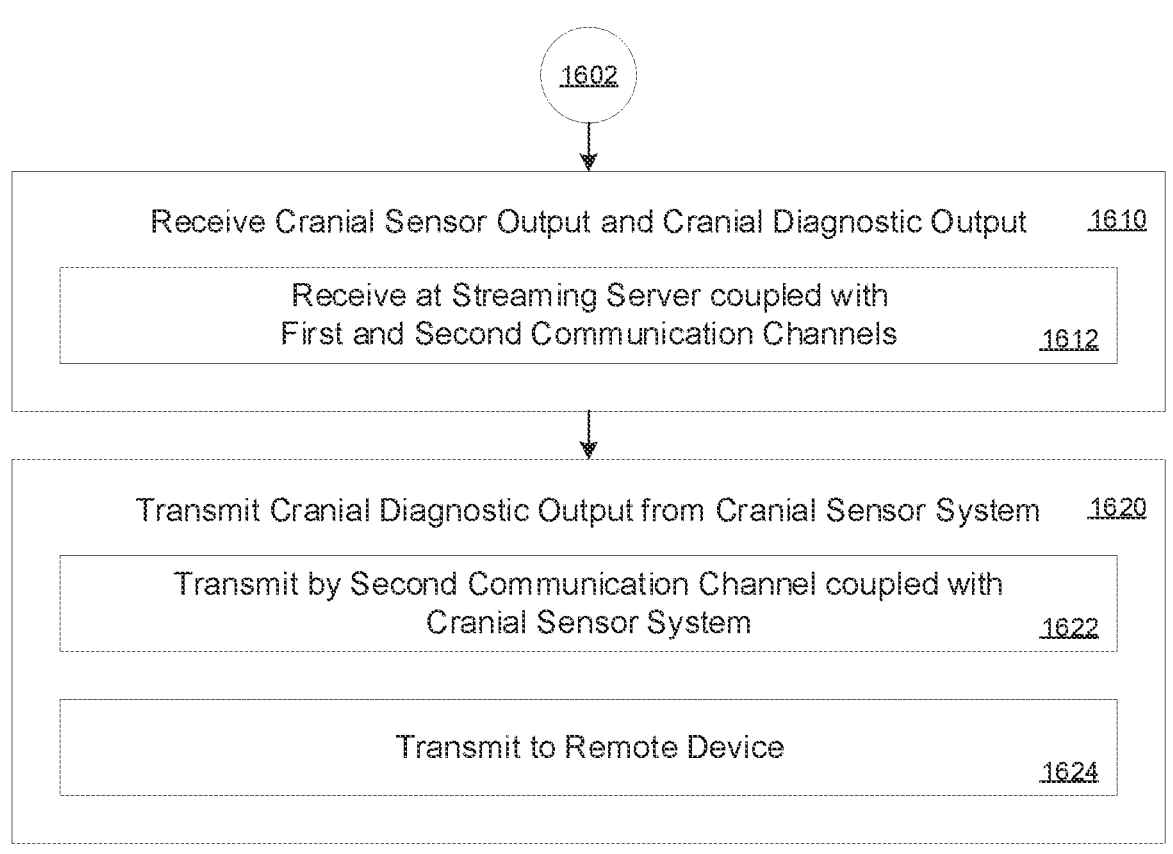

FIG. 16 illustrates an example method of remote transmission by a cranial sensor system, in accordance with present implementations.

DETAILED DESCRIPTION

The present implementations will now be described in detail with reference to the drawings, which are provided as illustrative examples of the implementations so as to enable those skilled in the art to practice the implementations and alternatives apparent to those skilled in the art. Notably, the figures and examples below are not meant to limit the scope of the present implementations to a single implementation, but other implementations are possible by way of interchange of some or all of the described or illustrated elements. Moreover, where certain elements of the present implementations can be partially or fully implemented using known components, only those portions of such known components that are necessary for an understanding of the present implementations will be described, and detailed descriptions of other portions of such known components will be omitted so as not to obscure the present implementations. Implementations described as being implemented in software should not be limited thereto, but can include implementations implemented in hardware, or combinations of software and hardware, and vice-versa, as will be apparent to those skilled in the art, unless otherwise specified herein. In the present specification, an implementation showing a singular component should not be considered limiting; rather, the present disclosure is intended to encompass other implementations including a plurality of the same component, and vice-versa, unless explicitly stated otherwise herein. Moreover, applicants do not intend for any term in the specification or claims to be ascribed an uncommon or special meaning unless explicitly set forth as such. Further, the present implementations encompass present and future known equivalents to the known components referred to herein by way of illustration.

Present implementations are directed to delivering a lossless, high-reliability signal representing the response from the cranial sensor system, providing a reliable and low-overhead transmission to the system. Present implementations are operable to transmit multiple channels of response from the cranial sensor system and provide multiple bandwidth capacities for the transmission to various remote applications. Conventional systems are limited to noninteractive and high-overheard techniques including sending video pixels corresponding to a screen capture or a virtual private network (VPN) connection to a particular clinical site device.

Present implementations are operable to provide at least a dual-channel output corresponding to response from a cranial sensor system by a first channel, and additional metadata, system information, system state, error states, and the like, by a second channel. The response from a cranial sensor system can be delivered in various modes corresponding to different levels of bandwidth. A "mirror" mode can correspond to a transmission by which all or substantially all of the response from the cranial sensor system can be transmitted by the first channel or the like to the remote application. An "essential" mode can correspond to a transmission by which a subset, portion, or the like, of the response from the cranial sensor system can be transmitted by the first channel or the like to the remote application. Because the response itself, and not a static or pixelated image of the image is transmitted, loss from video compression, artifacts, and the like can be advantageously reduced or eliminated. Thus, a technological solution for real-time transmission and remote presentation of response from a cranial sensor system is provided.

Present implementations can transmit lossless response from a cranial sensor system by a cloud gateway at the cranial sensor system to a remote application by a streaming server. The streaming server can be operatively coupled to the cloud gateway by a first channel including TCD response from the cranial sensor system and a sensor channel including response associated therewith. Because the system can transmit the TCD data directly to the streaming server, signal loss and degradation is substantially eliminated and bandwidth requirements for transmission are substantially reduced. Because TCD response, and the like, are highly sensitive and require nuanced analysis, any small variation the signal caused by signal loss, signal artifacts, and the like, can appear at a remote site as a false signal characteristic. In accordance with present implementations, medical personnel making patient care or emergency response decisions can remotely obtain response free of such loss and artifacts so as to prevent misdiagnosis based on an inaccurate signal presentation at a remote application.

Present implementations are directed to a scalable system of lossless transmission and remote presentation of response of a cranial sensor system. Present implementations can advantageously including a streaming server system including more than one streaming server system, in addition a single streaming server configuration. Implementations including multiple streaming servers can support multiple organizations, clinical sites, hospital sites, hospital systems, and the like. As one example, a single organization or the like can be coupled with one or more streaming application programming interfaces (APIs). Each streaming API can, in turn, be coupled with one or more cranial sensor systems. Thus, each streaming API can provide response data from one or more correspondingly coupled cranial sensor systems to one or more authorized remote applications at remote devices.

Figure 1:
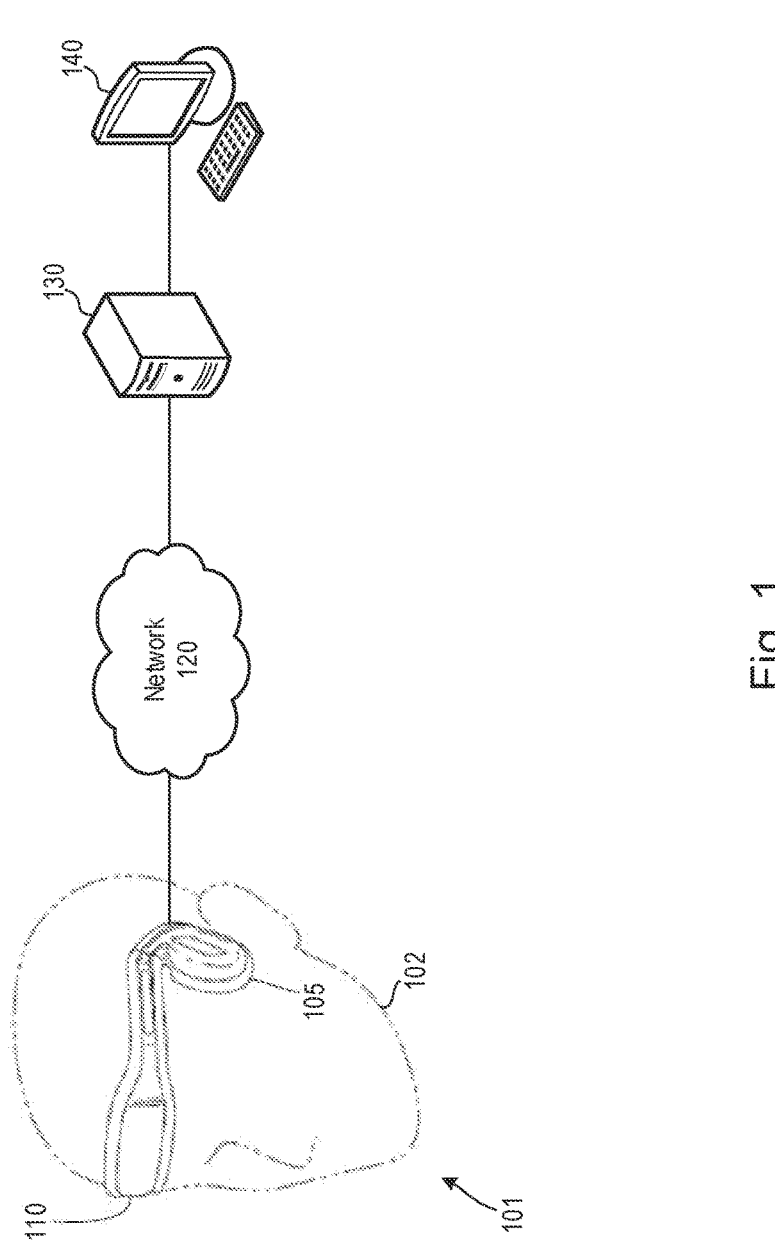
FIG. 1 illustrates an example system coupled with a cranial sensor system, in accordance with present implementations.

FIG. 1 illustrates an example cranial sensor system, in accordance with present implementations. As illustrated by way of example in FIG. 1, a cranial sensor system 100 includes at least a headset device 110, a controller 130, and an output device 140. The controller can be positioned between the headset and a network system, interface, and the like.

The headset device 110 is a TCD ultrasound device configured to emit and measure acoustic energy in a head 102 of a patient 101. An example of the headset device 110 is a supine headset device. The headset device 110 includes at least one probe 105 (e.g., at least one ultrasound probe) configured to emit and measure ultrasound acoustic energy in the head 102. For example, the probe 105 includes at least one TCD scanner, which can automatically locate the middle cerebral artery (MCA) in some arrangements. At least one probe 105 can be positioned in a temporal window region (temple) of the head 102 to collect the ultrasound data. In other arrangements, the probe can be positioned over different acoustic windows such as the transorbital window or the suboccipital window. In some arrangements, headset 110 includes two ultrasound probes 105, which can be placed on the temporal window region on both sides of the head 102. A headband, strap, Velcro®, hat, helmet, or another suitable wearable structure of the like connects the two probes in such arrangements. A lubricating gel can be applied between the head 102 and the probe 105 to improve acoustic transmission.

The controller 130 is configured to receive the ultrasound data outputted by the headset device 110 and to generate CBFV waveforms that correspond to the ultrasound data. In that regard, the probe 110 is operatively coupled to the controller 130 via a suitable network 120 to send the ultrasound data to the controller 130. The network 120 can be wired or wireless (e.g., 802.11X, ZigBee, Bluetooth®, Wi-Fi, or the like). The controller 130 can further perform signal processing functions to determine and display morphological indicators corresponding to the CBFV waveforms to facilitate a physician, clinician, technician, or care provider with diagnosis and/or to adjust the positioning of the headset device 110 and the probe 105. Further, as described, the headset device 110 can automatically adjust the position and orientation of the probe 105 responsive to determination that the probe 105 is not optimally placed based on the morphological indicators in the manner described herein. In some arrangements, the controller 130, the output device 140, and a portion of the network 120 are incorporated into a single device (e.g., a touchscreen tablet device).

In some arrangements, the output device 140 includes any suitable device configured to display information, results, messages, and the like to an operator (e.g., a physician, clinician, technician, or care provider) of the cranial sensor system 100. For example, the output device 140 includes but is not limited to, a monitor, a touchscreen, or any other output device configured to display the CBFV waveforms, the morphology indicators, and the like for facilitating diagnosis and/or the positioning of the headset device 110 and the probe 105 relative to the head 102 in the manner described.

Figure 2:
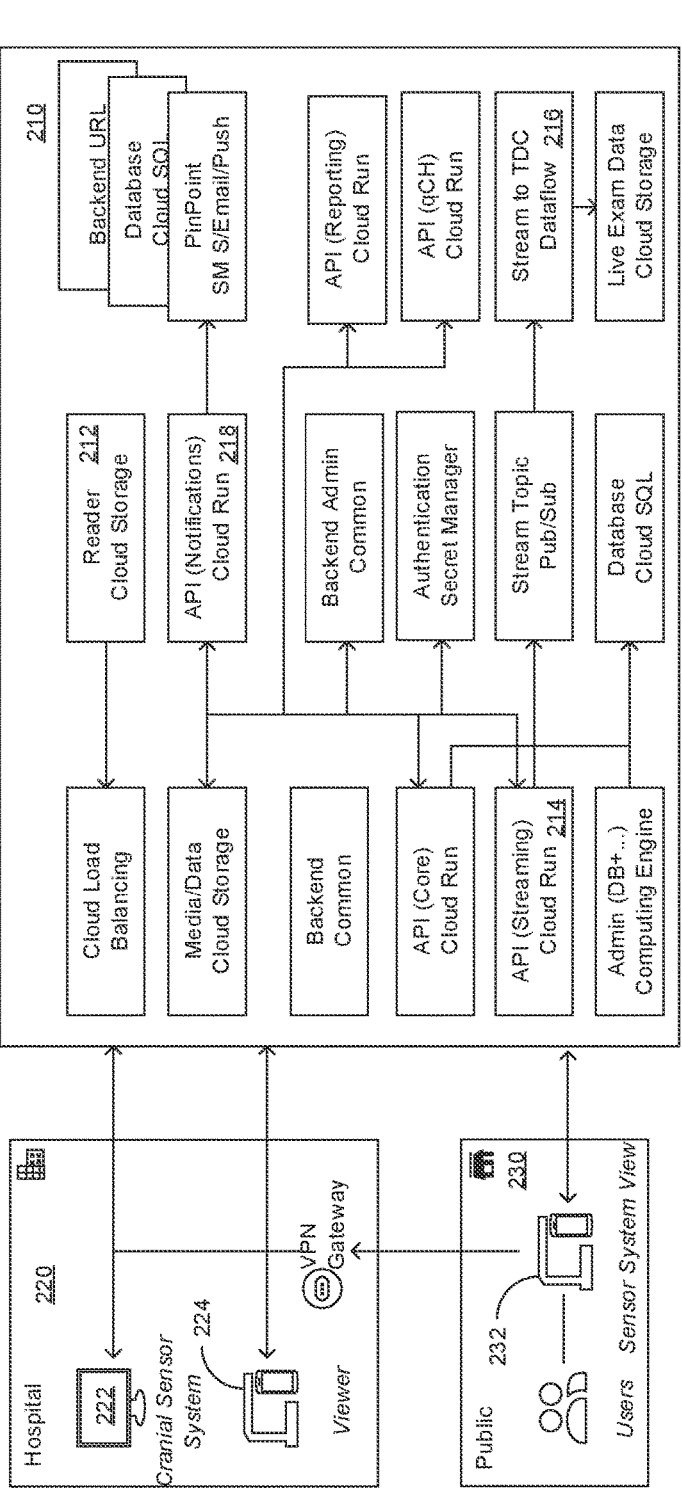
FIG. 2 illustrates an example system architecture for a cranial sensor system, in accordance with present implementations.

FIG. 2 illustrates an example system architecture for a cranial sensor system, in accordance with present implementations. As illustrated by way of example in FIG. 2, an example system architecture 200 includes at least a server system 210, a hospital system 220, and a public system 230. The server system 210 can include at least a reader cloud storage 212, a streaming interface 214, a stream processor 216, and a notification processor 218.

The reader cloud storage 212 can store data associated with the system 200. The reader cloud storage 212 can include one or more hardware memory devices to store binary data, digital data, or the like. The reader cloud storage 212 can include one or more electrical components, electronic components, programmable electronic components, reprogrammable electronic components, integrated circuits, semiconductor devices, flip flops, arithmetic units, or the like. The reader cloud storage 212 can include at least one of a non-volatile memory device, a solid-state memory device, a flash memory device, and a NAND memory device. The reader cloud storage 212 can include one or more addressable memory regions disposed on one or more physical memory arrays. A physical memory array can include a NAND gate array disposed on, for example, at least one of a particular semiconductor device, integrated circuit device, and printed circuit board device.

The streaming interface 214 can translate instructions between a first structure compatible with a hospital system 220 or any component thereof, and a public system 230 or any component thereof. For example, the streaming interface 214 can include an application programming interface (API) compatible with the hospital system 230. The streaming interface 214 can conduct unidirectional or bidirectional communication between a device of the hospital system 220 and a device of the public system 230. The streaming interface 214 can provide communication in one or more transmission modes. For example, a transmission mode can include a particular bit rate, set of metrics, or any combination thereof. For example, a transmission mode can include one or more restrictions on ranges of bit rates, metrics, or any combination thereof. A metric or set of metrics can correspond to one or more sensor inputs, objects corresponding to particular sensor inputs, channels corresponding to particular sensor inputs, or any combination thereof. For example, the streaming interface 214 can obtain a flag corresponding to a particular transmission mode or indicating a transmission mode via a field thereof. For example, the streaming interface 214 can select or deselect receiving or processing of particular fields thereof, in response to detecting a flag corresponding to a particular transmission mode or indicating a transmission mode.

The stream processor 216 can transmit and receive particular stream content between a hospital system 220 and a public system 230. The stream processor 216 can transmit data representing activity of the hospital system 220 or any component thereof, based on data received from the streaming interface 214. For example, the stream processor 216 can transmit data from the hospital system 220 corresponding to a subset of fields received by the hospital system 220 in connection with a particular cranial sensor system, in response to an indication by the streaming interface 214 of an essential transmission mode. For example, an essential transmission mode can correspond to an indication of transmission of less or fewer than all data or types of data transmitted by the hospital system 220 or a particular cranial sensor system thereof. For example, the stream processor 216 can transmit data from a particular cranial sensor system at a lower bitrate in an essential mode than a bitrate in a mirror mode. For example, the stream processor 216 can transmit data from a particular cranial sensor system at a lower granularity in an essential mode than a bit granularity rate in a mirror mode. For example, a granularity can correspond to a precision of a sensor output. For example, the stream processor 216 can transmit data from the hospital system 220 corresponding to all fields received by the hospital system 220 in connection with a particular cranial sensor system, in response to an indication by the streaming interface 214 of a mirror transmission mode. For example, a mirror transmission mode can correspond to an indication of transmission of all or more data or types of data transmitted by the hospital system 220 or a particular cranial sensor system thereof, as compared to an essential transmission mode.

The notification processor 218 can transmit and receive instructions to the public system 230 based on activity of one or more of the streaming interface 214 and the stream processor 216. For example, the notification processor 218 can transmit instructions to indicate a transmission mode at a user interface coupled with or integrated with the public system 230.

The hospital system 220 can include one or more computing devices located physically at, adjacent to, or within a medical facility. For example, a computing device can be located adjacent to a medical facility where a latency between the computing device and a computing device located at the medical facility is at or below a predetermined threshold latency. The hospital system 220 can include a cranial sensor system 222 and a viewer device 224. The cranial sensor system can correspond to the cranial sensor system 100.

The public system 230 can 220 can include one or more computing devices located physically away from, or outside a medical facility. For example, a computing device can be located away from a medical facility where a latency between the computing device and a computing device located at the medical facility is at or above the predetermined threshold latency. The public system 230 can include one or more computing devices 232, one or more networks coupled with one or more computing devices 232, or any combination thereof. A computing device 232 can include, for example, a smartphone, tablet, e-reader, laptop computer, desktop computer, or any combination thereof.

Figure 3:
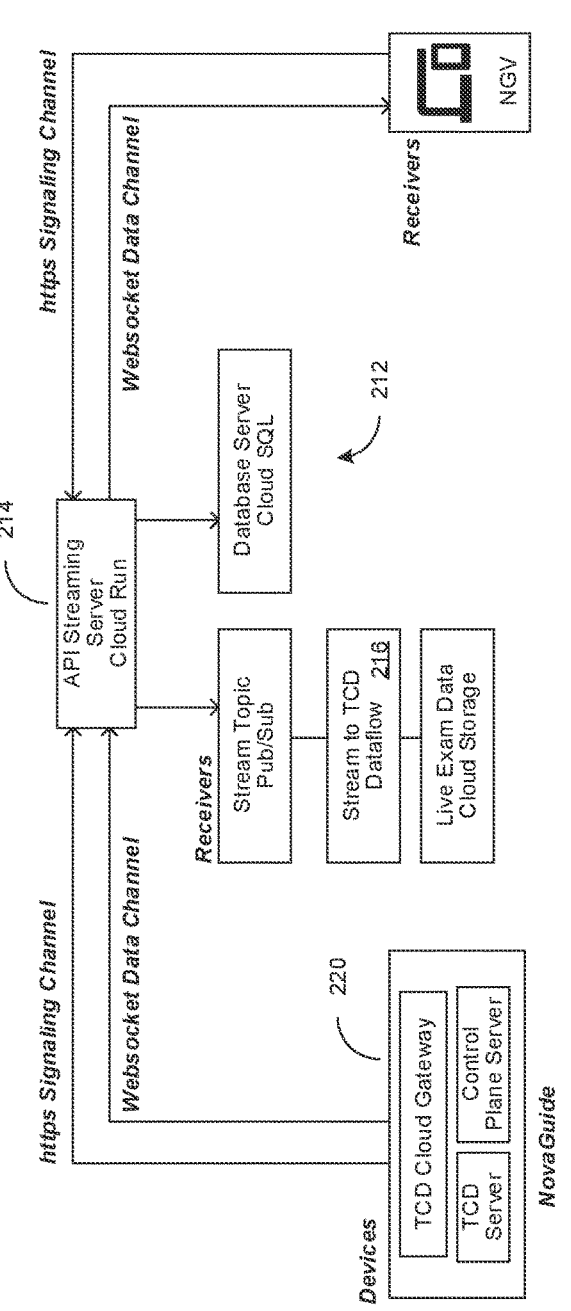
FIG. 3 illustrates an example real-time streaming architecture for a cranial sensor system, in accordance with present implementations.

FIG. 3 illustrates an example real-time streaming architecture for a cranial sensor system, in accordance with present implementations. As illustrated by way of example in FIG. 3, an example streaming architecture 300 can include at least the reader cloud storage 212, the streaming interface 214, the stream processor 216, and hospital system 220. The TCD server can obtain TCD response signals from a cranial sensor system and transmit the TCD response signals to the streaming interface 214 by the signaling channel. The control plane server can obtain any signal, data, or the like associated with the TCD signals, the cranial sensor system, the hospital site, the clinical site, the patient, or the like, and transmit the that signal, data, or the like to streaming interface 214 by the web socket data channel. As one example, control plane data can include one or more of user input to the cranial sensor system and robotic output of the cranial sensor system. As one example, user input can include changing a vessel name in the UI. As another example, robot output can include position and orientation of the robot sensors. It is to be understood that the signaling channel and the web socket data channel can advantageously reduce bandwidth required to transmit a response from the cranial sensor system, and can also advantageously achieve lossless and real-time or substantially real-time transmission of the response. As one example, the architecture 300 can achieve a substantially 900 kpbs bandwidth transmission in essential mode and a substantially 8 Mbps bandwidth transmission in mirror mode, reducing bandwidth consumption significantly from conventional system constrained in the 10-15 Mbps bandwidth range for lossy transmissions. The transmitted response can include representations of visual waveforms, audio waveforms, geometric relationships of various cranial structures, pressures, temperatures, and the like.

The signaling channel and the web socket data channel can be operable to communicatively couple the streaming interface 214 with the hospital system 220. In some implementations, one or more of the signaling channel and the web socket data channel are operable to communicate one or more instructions, signals, conditions, states, or the like. In some implementations, one or more of the signaling channel and the web socket data channel include one or more digital, analog, or like communication channels, lines, traces, or the like. As one example, one or more of the signaling channel and the web socket data channel include at least one serial or parallel communication line among multiple communication lines of a communication interface. In some implementations, one or more of the signaling channel and the web socket data channel include one or more wireless communication devices, systems, protocols, interfaces, or the like. In some implementations, one or more of the signaling channel and the web socket data channel include one or more logical or electronic devices including but not limited to integrated circuits, logic gates, flip flops, gate arrays, programmable gate arrays, and the like. In some implementations, one or more of the signaling channel and the web socket data channel are include ones or more telecommunication devices including but not limited to antennas, transceivers, packetizers, wired interface ports, and the like.

Figure 4:
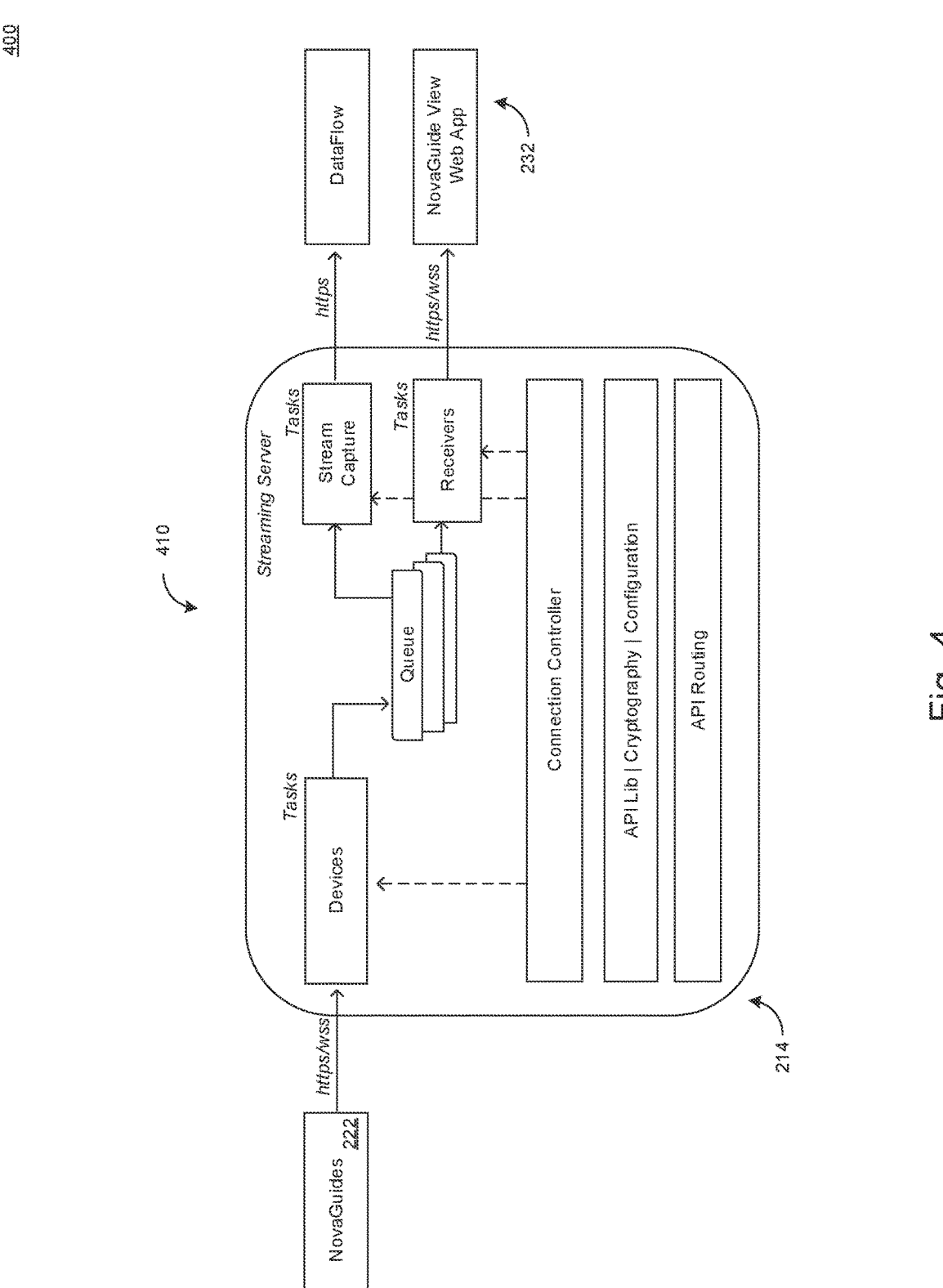
FIG. 4 illustrates an example streaming server system architecture for a cranial sensor system, in accordance with present implementations.

FIG. 4 illustrates an example streaming server system architecture for a cranial sensor system, in accordance with present implementations. As illustrated by way of example in FIG. 4, an example streaming server system 400 includes at least the streaming server 410.

The streaming server 410 can include a device interface, a streaming queue, a stream capture interface, a connection controller, an API library layer, a cryptography layer, a configuration layer, and an API layer. One or more of the elements of FIG. 4 can include one or more logical or electronic devices including but not limited to integrated circuits, logic gates, flip flops, gate arrays, programmable gate arrays, and the like. In some implementations, the cranial sensor system or systems can correspond to one or more NovaGuide™ devices or the like. The device interface can be operatively coupled to the cranial sensor system by one or more of the signaling channel and the web socket data channel. Thus, in some implementations, the device interface receives both TCD server output and control plane server output from the cranial sensor systems. The device interface comprise a plurality of device interfaces operatively coupled with the connection controller to obtain and transmit one or more streams specifically associated with respective ones of the cranial sensor systems, in implementations include a plurality of cranial sensor systems. Each of the streams can be associated with, added to, or the like, one or more streaming queues.

The stream capture interface can obtain stream content from one or more of the streaming queues in coordination with the receiver interface. As one example, the receiver interface can obtain one or more requested streams from one or more corresponding any consuming applications not limited to view web applications, and can communication with the stream capture device to retrieve the stream or streams associated with each corresponding request. The stream capture interface can access the streaming queues and can transmit streaming content from a corresponding one or more of the receivers to complete the request at the streaming server. The receiver can then transmit the streaming content to the web application. In some implementations, the receiver can transmit the streaming content to a remote device executing the web application or a corresponding native application, service, or the like, to complete the request for the web application. In some implementations, the receiver can transmit the streaming content by an encrypted channel, communication, or the like. The stream capture interface can transmit the stream content by a dataflow communication channel accessible to the web application. In some implementations, the receiver can transmit a token, identifier, or the like to the web application indicating an address, identifier, credential, or the like, allow the web application to access and obtain the requesting stream content from the dataflow communication channel. The streaming server 410 can control, direct, manage, monitor, and the like, streaming by the connection controller, in response to communication received and transmitted by the API library and the API routing layers. The API routing layers can provide command and request translation for commands and requests associated with the API routing layer.

Figure 5:
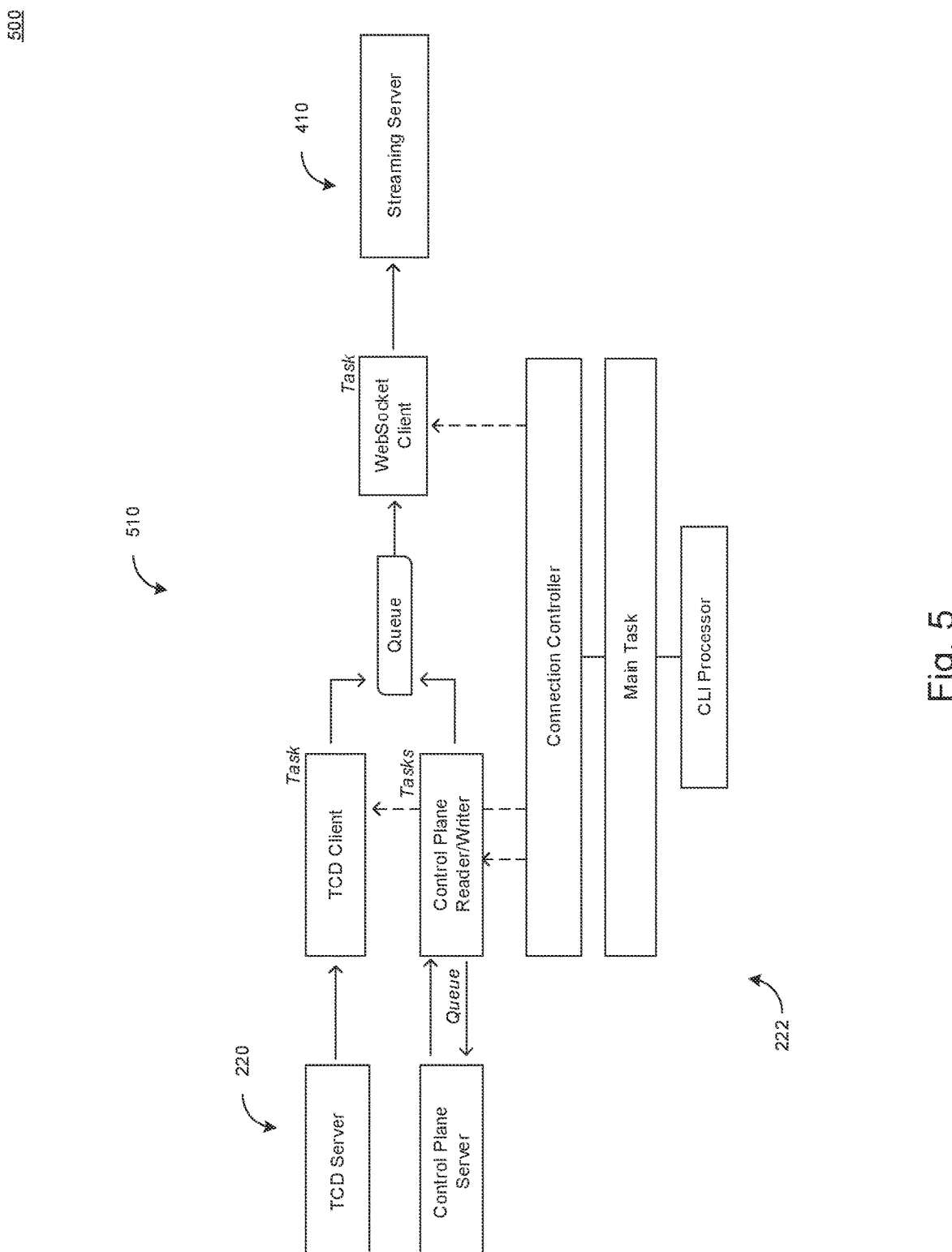
FIG. 5 illustrates an example gateway system architecture for a cranial sensor system, in accordance with present implementations.

FIG. 5 illustrates an example gateway system architecture for a cranial sensor system, in accordance with present implementations. As illustrated by way of example in FIG. 5, an example gateway system architecture 500 includes at least the streaming server 410 and the cloud gateway 510.

The cloud gateway 510 can include at least a TCD client interface, a control plane reader/writer interface, a web socket client, a connection controller, a main task layer, a gateway queue and a CLI processor layer. The TCD client can be operatively coupled with the TCD server and can be operatively coupled to the TCD server to obtain one or more responses from the cranial sensor system. The TCD server can be integrated with or coupled with the cranial sensor system, and can include one or more physical connectors, logical interfaces, electrical connectors, electromechanical connectors, or the like, with various sensors, processors, and the like of the cranial sensor system. The TCD client interface and the cloud gateway 510 can thus advantageously interface directly with one or more cranial sensor systems to obtain raw response data, signals, and the like in one or more of a real-time and lossless fashion. Correspondingly, the control plane server can be integrated with or coupled with the cranial sensor system, and can include one or more physical connectors, logical interfaces, electrical connectors, electromechanical connectors, or the like, with various sensors, processors, and the like of the cranial sensor system. The control plane reader/writer interface and the cloud gateway 510 can thus also advantageously interface directly with one or more cranial sensor systems to obtain metadata, system information, patient information, clinical site information, response data, signals, and the like in one or more of a real-time and lossless fashion.

In some implementations, the TCD gateway can combine output from the TCD client interface and the control plane reader/writer interface and provide the combine response signal to the gateway queue. The web socket client interface can obtain stream content from the gateway queue and can transmit at least one selected stream content to the streaming server 410. The streaming server 410 can obtain the combined stream content by the signaling channel and the web socket data channel. In some implementations, the web socket client is operable to obtains the combined stream content from the gateway queue and separate the combined stream content into a content stream for the signaling channel and a second content stream for the web socket data channel. Alternatively, in some implementations, the web socket client can obtains independent streams from the gateway queue, where streams from the TCD client are added to the queue separately. The separate streams can be associated with each other by identifier, address, token, and the like. It is to be understood that that the TCD server and the TCD client interface are not limited to TCD responses from the cranial sensor systems, and can be associated with any response related to cranial sensors with respect to the cranial sensor system or the like.

Figure 6:
FIG. 6 illustrates a first example communication method for a cranial sensor system, in accordance with present implementations.

FIG. 6 illustrates a first example communication method for a cranial sensor system, in accordance with present implementations. In some implementations, at least one of the server system 210, corresponding to a cloud system, and the cloud gateway 510, corresponding to a sensor system performs method 600 according to present implementations.

The sensor system 210 can POST units/streaming/authorization from a control plane of the sensor system 510 to a core API of the cloud system 210. The cloud system 220 can send an OK or ACK signal from the core API of the cloud system 220 to the control plane of the sensor system 510. The sensor system 210 can send a launch gateway instruction by a token from the control plane of the sensor system 510 to a TCD gateway of the cloud system 210. The sensor system 210 can connect the TCD gateway of the sensor system 510 to the control plane of the sensor system 510. The sensor system 210 can send an OK or ACK signal to the TCD gateway of the sensor system 510 from the control plane of the sensor system 510. The sensor system 210 can send a web socket connect signal from the TCD gateway of the sensor system 510 to a streaming API of the cloud system 210. The cloud system 220 can send an OK or ACK signal from the streaming API of the cloud system 220 to the TCD gateway of the sensor system 510. The sensor system 210 can send a TCP connect signal from the TCD gateway of the sensor system 510 to a TCD server of the sensor system 510. The sensor system 210 can send an OK or ACK signal to the TCD gateway of the sensor system 510 from the TCD server of the sensor system 510.

The sensor system 210 can send control plane data from the control plane of the sensor system 510 to the TCD gateway of the sensor system 510. The sensor system 210 can send control plane data from to the TCD gateway of the sensor system 510 to the streaming API of the cloud system 210. The sensor system 210 can send TCD data from the TCD server of the sensor system 510 to the TCD gateway of the sensor system 510. The sensor system 210 can send TCD data from to the TCD gateway of the sensor system 510 to the streaming API of the cloud system 210.

Figure 7:
FIG. 7 illustrates a second example communication method for a cranial sensor system, in accordance with present implementations.

FIG. 7 illustrates a second example communication method for a cranial sensor system, in accordance with present implementations. In some implementations, at least one of the reader cloud storage 212, corresponding to a reader, and the server system 210, corresponding to a cloud system, performs method 700 according to present implementations.

The reader system 212 can send a GET signal with organization/streaming/authorization data to the core API of the cloud system 210. The cloud system 210 can send an OK or ACK signal to the reader system 212 from the core API. The reader system 212 can send a GET signal for streaming devices to the streaming API of the cloud system 210. The cloud system 210 can send an OK or ACK signal to the reader system 212 from the streaming API. The reader system 212 can send a web socket connect signal to the streaming API of the cloud system 210. The cloud system 210 can send an OK or ACK signal to the reader system 212 from the streaming API. The cloud system 210 can send control plane data and TCD data to the reader system 212 from the streaming API.

Figure 8:
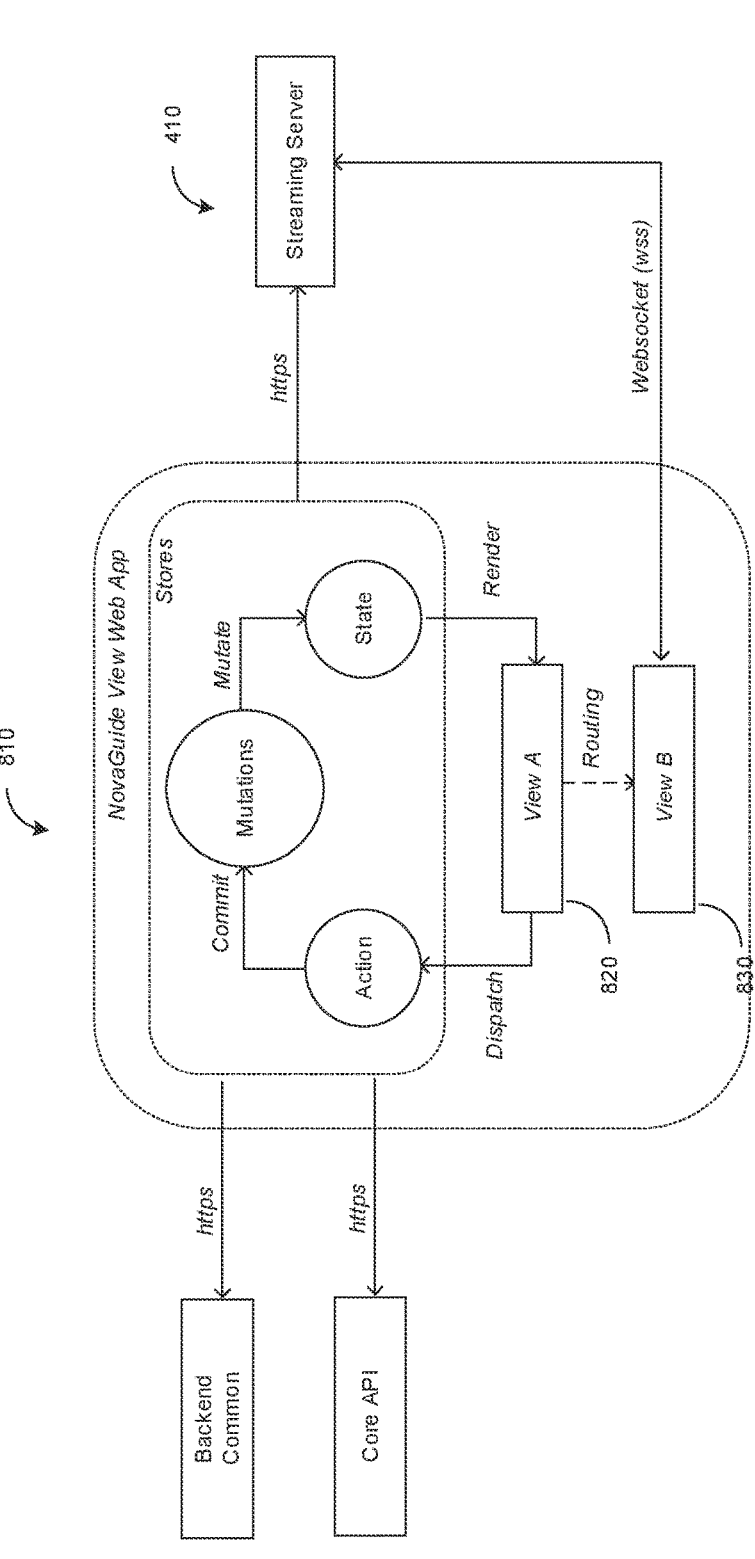
FIG. 8 illustrates a first example user interface system for a cranial sensor system, in accordance with present implementations.

FIG. 8 illustrates a first example user interface system for a cranial sensor system, in accordance with present implementations. As illustrated by way of example in FIG. 8, an example user interface system 800 includes at least the streaming server 410, a web application object 810, a first view object 820, and a second view object 830. The user interface system 800 can be presented at a display of a remote device or the like. The display device can be operable to display one or more elements of the user interface system 800. In some implementations, the display device includes an electronic display. In some implementations, the electronic display includes a liquid crystal display (LCD), a light-emitting diode (LED) display, an organic light-emitting diode (OLED) display, or the like.

Figure 9:
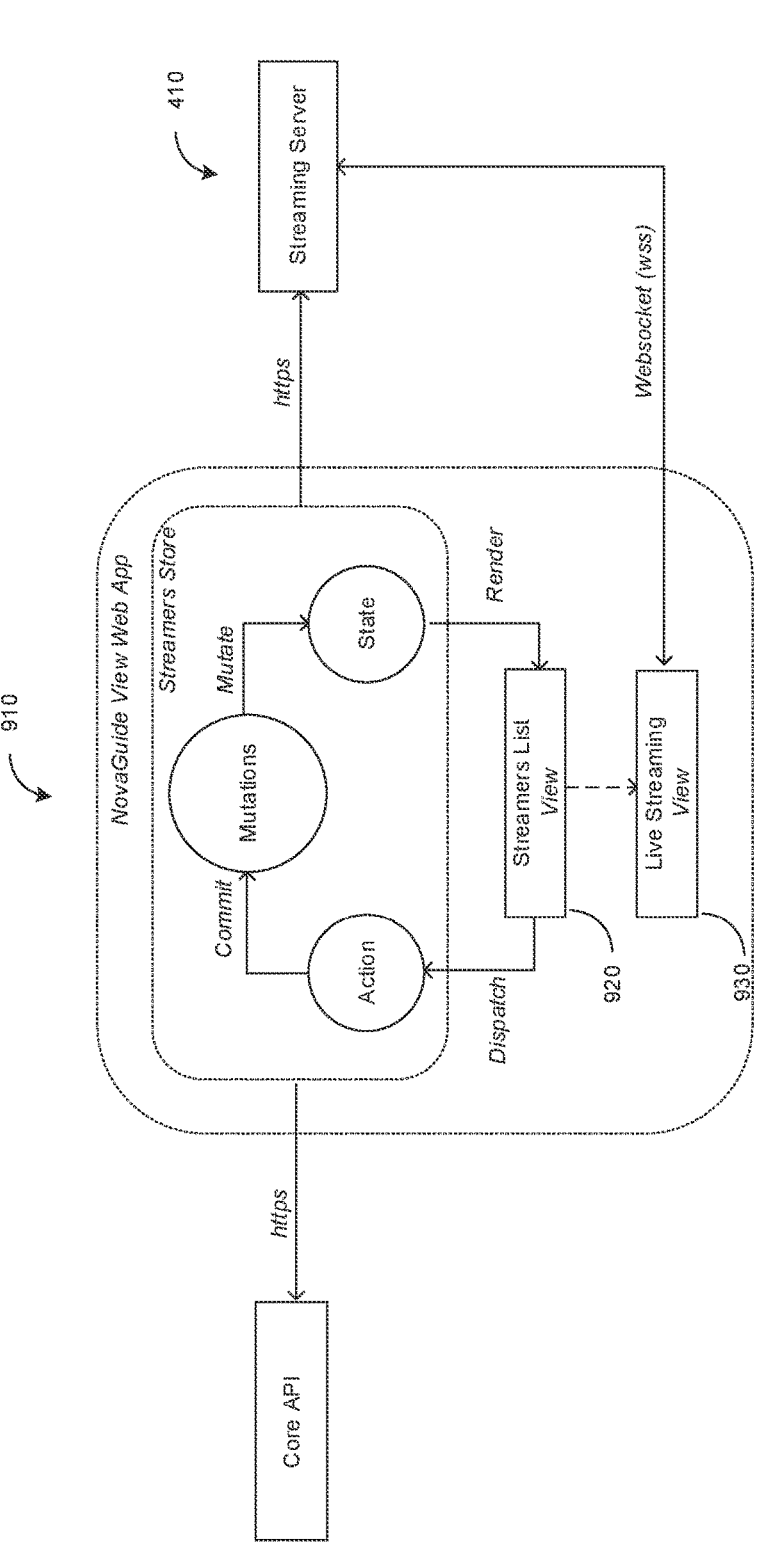
FIG. 9 illustrates a second example user interface system for a cranial sensor system, in accordance with present implementations.

FIG. 9 illustrates a second example user interface system for a cranial sensor system, in accordance with present implementations. As illustrated by way of example in FIG. 9, an example user interface system 900 includes at least the streaming server 410, a web application object 910, a first view object 920, and a second view object 930. The user interface system 900 can be presented at a display of a remote device or the like. The display device can be operable to display one or more elements of the user interface system 900. In some implementations, the display device includes an electronic display. In some implementations, the electronic display includes a liquid crystal display (LCD), a light-emitting diode (LED) display, an organic light-emitting diode (OLED) display, or the like.

Figure 10:
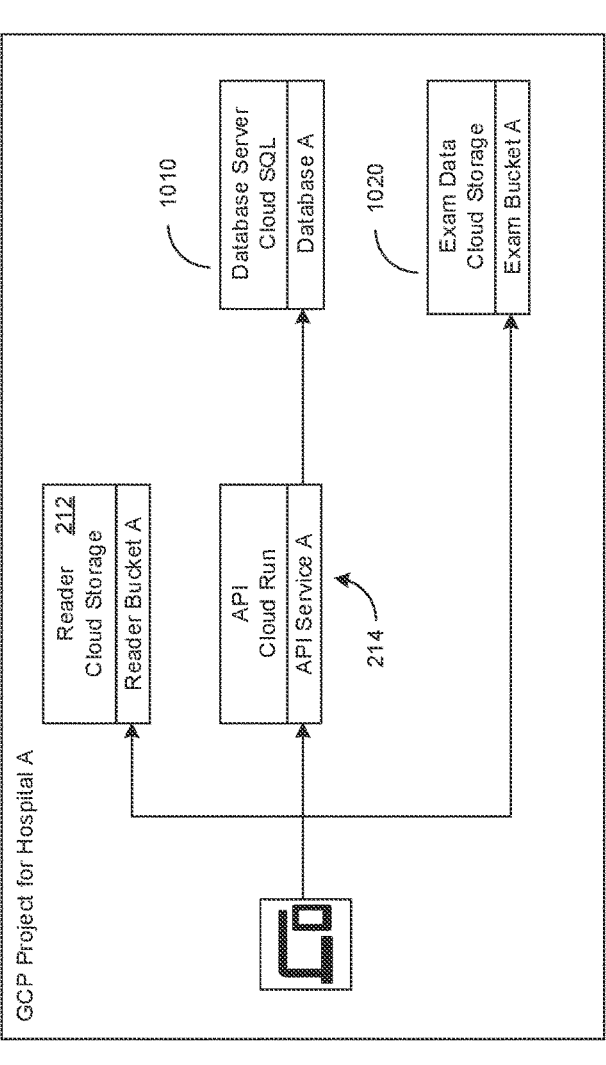
FIG. 10 illustrates a first example hospital site system for a cranial sensor system, in accordance with present implementations.

FIG. 10 illustrates a first example hospital site system for a cranial sensor system, in accordance with present implementations. As illustrated by way of example in FIG. 10, an example hospital site system 1000 includes at least a first database server 1010 and a first exam data storage component 1020.

For example, the hospital site system 1000 can include Hospital A, and an API service A compatible with Hospital A and with the streaming interface 214. For example, the API service A can be compatible only with, restricted to compatibility with, or restricted to operation with Hospital A. The reader 212 can include a corresponding logical or physical and non-tangible memory corresponding to Reader Bucket A. For example, Reader Bucket A can be compatible only with, restricted to compatibility with, or restricted to operation with Hospital A. The first database server 1010 can include a corresponding logical or physical and non-tangible memory corresponding to Database A. For example, Database A can be compatible only with, restricted to compatibility with, or restricted to operation with Hospital A. The first exam data storage component 1020 can include a corresponding logical or physical and non-tangible memory corresponding to Exam Bucket A. For example, Exam Bucket A can be compatible only with, restricted to compatibility with, or restricted to operation with Hospital A.

Figure 11:
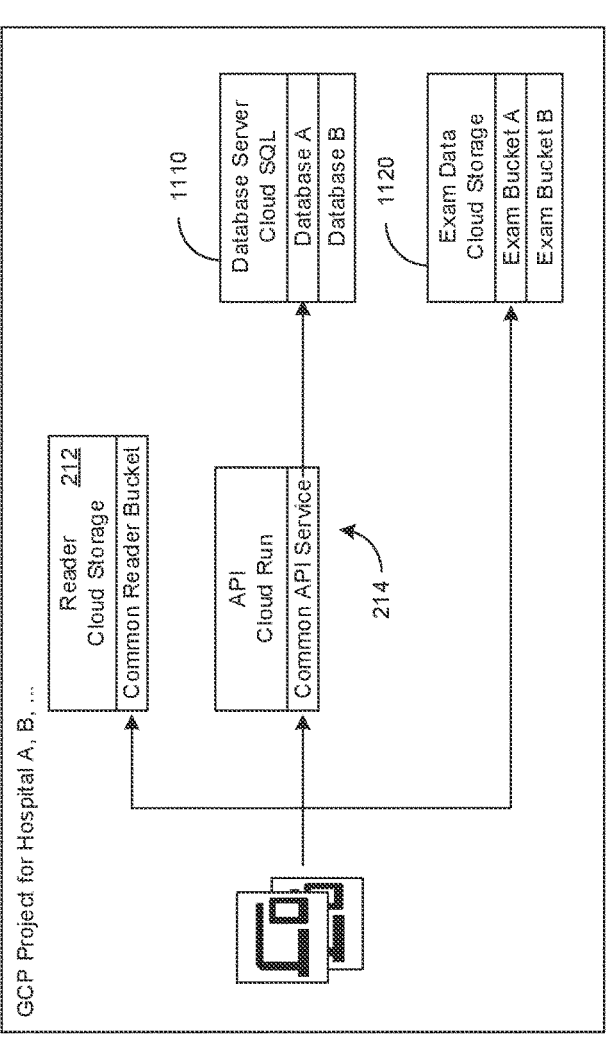
FIG. 11 illustrates a second example hospital site system for a cranial sensor system, in accordance with present implementations.

FIG. 11 illustrates a second example hospital site system for a cranial sensor system, in accordance with present implementations. As illustrated by way of example in FIG. 11, an example hospital site system 1100 includes at least a first database server 1110 and a first exam data storage component 1120.

For example, the hospital site system 1100 can include Hospital A, Hospital B, and a common API service compatible with Hospital A, Hospital B, and the streaming interface 214. For example, the common API service can be compatible with or operable with Hospital A and Hospital B. The reader 212 can include a corresponding logical or physical and non-tangible memory corresponding to a common Reader Bucket. For example, the common Reader Bucket can be compatible with or operable with Hospital A and Hospital B. The first database server 1110 can include a corresponding logical or physical and non-tangible memory corresponding to Database A, and a corresponding logical or physical and non-tangible memory corresponding to Database B. For example, Database A can be compatible only with, restricted to compatibility with, or restricted to operation with Hospital A. For example, Database B can be compatible only with, restricted to compatibility with, or restricted to operation with Hospital B. The first exam data storage component 1120 can include a corresponding logical or physical and non-tangible memory corresponding to Exam Bucket A, and a corresponding logical or physical and non-tangible memory corresponding to Exam Bucket B. For example, Exam Bucket A can be compatible only with, restricted to compatibility with, or restricted to operation with Hospital A. For example, Exam Bucket B can be compatible only with, restricted to compatibility with, or restricted to operation with Hospital B.

FIG. 12 illustrates a third example hospital site system for a cranial sensor system, in accordance with present implementations. As illustrated by way of example in FIG. 12, an example hospital site system 1200 includes at least a first database server 1210 and a first exam data storage component 1220.

For example, the hospital site system 1200 can include Hospital A, Hospital B, and a common API service compatible with Hospital A, Hospital B, and the streaming interface 214. For example, the common API service can be compatible with or operable with Hospital A and Hospital B. The reader 212 can include a corresponding logical or physical and non-tangible memory corresponding to a common Reader Bucket. For example, the common Reader Bucket can be compatible with or operable with Hospital A and Hospital B. The first database server 1210 can include a corresponding logical or physical and non-tangible memory corresponding to Database AB. For example, Database AB can be compatible with or operable with Hospital A and Hospital B. The first exam data storage component 1220 can include a corresponding logical or physical and non-tangible memory corresponding to Exam Bucket A, and a corresponding logical or physical and non-tangible memory corresponding to Exam Bucket B. For example, Exam Bucket A can be compatible only with, restricted to compatibility with, or restricted to operation with Hospital A. For example, Exam Bucket B can be compatible only with, restricted to compatibility with, or restricted to operation with Hospital B.

FIG. 13 illustrates a first streaming architecture for a cranial sensor system, in accordance with present implementations. As illustrated by way of example in FIG. 13, an example streaming architecture 1300 includes at least a first organizational streaming API 1310 and a second organizational streaming API 1320. For example, the first organizational streaming API 1310 can couple with various APIs and databases of the second organizational streaming API 1320. Thus, the first organizational streaming API 1310 can include a simplified and networked interface architecture that can be compatible with and integrated with various APIs and databases of the second organizational streaming API 1320.

FIG. 14 illustrates a second streaming architecture for a cranial sensor system, in accordance with present implementations. As illustrated by way of example in FIG. 14, an example streaming architecture 1400 includes at least a plurality of streaming APIs 1410, a plurality of cranial sensor systems 1420, and a plurality of remote applications 1430. It is to be understood that the numbers of each of the streaming APIs 1410, the cranial sensor systems 1420, and the remote applications 1430 are not limited to the example shown, and can be modified to any number. It is to be further understood that that the streaming APIs 1410 are not limited to the same N connections to corresponding remote applications 1430, and each of the streaming APIs 1410 can be connected to a different number of remote applications 1430 independent of any other one or more of the streaming APIs 1410.

Various ones of the remote applications 1430, remote devices, executing the remote applications 1430, and the like, can be associated with corresponding default settings, restrictions, and the like. Various, settings, restrictions, and the like can be associated with one or more of network characteristics, network connection characteristics, device characteristics, device identity, user characteristics, user identity, and the like. As one example, a device or application receiving a mirror mode communication can access additional signals representations, metadata, and the like than the device or another device receiving an essential mode communication from the same or different cranial sensor system. As another example, a device or application associated with a first user or user type and can access additional signals representations, metadata, and the like than the device or another device associated with a second user or user type accessing a communication from the same or different cranial sensor system. The user or user type can be an anesthesiologist having a lower access level for one or more responses of the cranial sensor system than a neurologist accessing the same cranial sensor system. As one example, the neurologist can be authorized to access a superset of responses, a greater range of one or more responses, or the like, than the anesthesiologist. As another example, the neurologist may access an entire TCD waveform, while the anesthesiologist can only access a magnitude of the waveform or a notification that the waveform has crossed a particular threshold or the like.

FIG. 15 depicts an example method of transmission by a cranial sensor system, in accordance with present implementations. At least one of the system 100 and the device 200 can perform method 1500.

At 1510, the method 1500 can select a transmission mode. At 1512, the method 1500 can select a mirror mode having a first bandwidth. For example, a mirror mode can correspond to transmission of all data produced at a cranial sensor system, all types of data produced at a cranial sensor system, transmission of data from a cranial sensor system at a maximum predetermined bandwidth, or any combination thereof. At 1514, the method 1500 can select an essential mode having second bandwidth lower than a first bandwidth. For example, an essential mode can correspond to transmission of a subset of data produced at a cranial sensor system, a subset of types of data produced at a cranial sensor system, transmission of data from a cranial sensor system at a predetermined bandwidth below a maximum predetermined bandwidth, or any combination thereof.

At 1520, the method 1500 can transmit a cranial sensor output from a cranial sensor system. At 1522, the method 1500 can transmit a cranial sensor output from a cranial sensor system by a first communication channel coupled with cranial sensor system. At 1524, the method 1500 can transmit a cranial sensor output from a cranial sensor system losslessly and in real-time. For example, lossless transmission can include transmission of numeric data, text data, binary data, or any combination thereof, directly representing particular values. For example, a lossy transmission can include transmission of a remote desktop feed or transmission of images that correspond to a screen capture or user interface capture. For example, a first communication channel can correspond to an API compatible with a cranial sensor output from a cranial sensor system. For example, the first communication channel can include a dedicated channel having a particular bandwidth meeting a minimum threshold to transmit waveforms corresponding to cranial sensor output in real-time or near-real-time over a distributed network system. A distributed network system can include, for example, the Internet or wide-area-network (WAN).

At 1530, the method 1500 can transmit a cranial diagnostic output from a cranial sensor system. At 1532, the method 1500 can transmit a cranial diagnostic output from a cranial sensor system by a second communication channel coupled with a cranial sensor system. At 1534, the method 1500 can transmit a cranial diagnostic output from a cranial sensor system losslessly and in real-time. For example, a second communication channel can correspond to an API compatible with a cranial diagnostic output from a cranial sensor system. For example, the first communication channel can include a dedicated channel having a particular bandwidth meeting a minimum threshold to transmit state information or activity information corresponding to the cranial sensor system in real-time or near-real-time over a distributed network system.

FIG. 16 depicts an example method of remote transmission by a cranial sensor system, in accordance with present implementations. At least one of the system 100 and the device 200 can perform method 1600. The method 1660 can continue from 1602. At 1610, the method 1600 can receive a cranial sensor output and a cranial diagnostic output. At 1612, the method 1600 can receive a cranial sensor output and a cranial diagnostic output at a streaming server coupled with a first communication channel and a second communication channel. For example, a streaming server can include a computing device coupled via a network to a cranial sensor system and a user device. For example, a streaming server can be remote from a cranial sensor system and a user device. At 1620, the method 1600 can transmit a cranial diagnostic output from a cranial sensor system. At 1622, the method 1600 can transmit a cranial diagnostic output from a cranial sensor system by a second communication channel coupled with a cranial sensor system. At 1624, the method 1600 can transmit a cranial diagnostic output from a cranial sensor system to a remote device.

The herein described subject matter sometimes illustrates different components contained within, or connected with, different other components. It is to be understood that such depicted architectures are illustrative, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically connectable and/or physically interacting components and/or wirelessly interactable and/or wirelessly interacting components and/or logically interacting and/or logically interactable components.

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Further, unless otherwise noted, the use of the words "approximate," "about," "around," "substantially," etc., mean plus or minus ten percent.

The foregoing description of illustrative implementations has been presented for purposes of illustration and of description. It is not intended to be exhaustive or limiting with respect to the precise form disclosed, and modifications and variations are possible in light of the above teachings or may be acquired from practice of the disclosed implementations. It is intended that the scope of the invention be defined by the claims appended hereto and their equivalents.

What is claimed is:

1. A system comprising:
a first communication channel operatively coupled with a cranial sensor system and operable to transmit, to a remote device, a cranial sensor output of a first data format, the first data format comprising raw data output comprising sensor response data generated by an ultrasonic sensor of the cranial sensor system, wherein the raw data output is associated with physiological measurements obtained by the ultrasonic sensor, and wherein the first communication channel is configured to losslessly transmit the cranial sensor output; and
a second communication channel separate from the first communication channel, operatively coupled with the cranial sensor system and operable to transmit, to the remote device, a diagnostic output of a second data format different from the first data format, the diagnostic output comprising at least one of metadata, system state data of the cranial sensor system, control plane data associated with operation of the cranial sensor system, and diagnostic data derived from the cranial sensor output, wherein at least one of the first communication channel and the second communication channel is operable to transmit in a mirror mode corresponding to a first bandwidth, and wherein at least one of the first communication channel and the second communication channel is operable to transmit in an essential mode corresponding to a second bandwidth less than the first bandwidth.

2. The system of claim 1, wherein the second communication channel transmits losslessly.

3. The system of claim 1, wherein at least one of the first communication channel and the second communication channel transmits in real-time.

4. The system of claim 1, wherein the cranial sensor output comprises Transcranial Doppler ultrasound (TCD) output.

5. The system of claim 1, wherein the remote device comprises at least one of a smartphone, tablet, personal computer, computer, a television, a smart television, a smart watch, and a connected smart watch.

6. The system of claim 1, further comprising:
a streaming server operatively coupled with the first communication channel, the second communication channel, the cranial sensor system, and the remote device, and operable to receive the cranial sensor output and the diagnostic output, and to transmit the cranial sensor output and the diagnostic output to the remote device.

7. The system of claim 6, wherein the streaming server is operatively coupled to a plurality of remote devices including the remote device, and wherein the streaming server is operable to transmit the cranial sensor output and the diagnostic output to one or more of the remote devices.

8. A method comprising:

transmitting, by a first communication channel operatively coupled with a cranial sensor system, to a remote device, a cranial sensor output of a first data format, the first data format comprising raw data output comprising sensor response data generated by an ultrasonic sensor of the cranial sensor system, wherein the raw data output is associated with physiological measurements obtained by the ultrasonic sensor, and wherein the first communication channel is configured to losslessly transmit the cranial sensor output; and transmitting, by a second communication channel separate from the first communication channel and operatively coupled with the cranial sensor system, to the remote device, a diagnostic output of a second data format different from the first data format, the diagnostic output comprising at least one of metadata, system state data of the cranial sensor system, control plane data associated with operation of the cranial sensor system, and diagnostic data derived from the cranial sensor output, wherein at least one of the first communication channel and the second communication channel is operable to transmit in a mirror mode corresponding to a first bandwidth, and wherein at least one of the first communication channel and the second communication channel is operable to transmit in an essential mode corresponding to a second bandwidth less than the first bandwidth.

9. The method of claim 8, wherein the second communication channel is configured to losslessly transmit the diagnostic output.

10. The method of claim 8, wherein at least one of the transmitting the cranial sensor output and the transmitting the diagnostic output comprises transmitting in real-time.

11. The method of claim 8, wherein the cranial sensor output comprises Transcranial Doppler ultrasound (TCD) output.

12. The method of claim 8, wherein the remote device comprises at least one of a smartphone, tablet, personal computer, computer, a television, a smart television, a smart watch, and a connected smart watch.

13. The method of claim 8, further comprising:

receiving, by a streaming server operatively coupled with the first communication channel, the second communication channel, the cranial sensor system, and the remote device, the cranial sensor output and the diagnostic output; and transmitting, by the streaming server, the cranial sensor output and the diagnostic output to the remote device.

14. The method of claim 13, wherein the streaming server is operatively coupled to a plurality of remote devices including the remote device, and wherein the streaming server is operable to transmit the cranial sensor output and the diagnostic output to one or more of the remote devices.

15. A non-transitory computer-readable medium comprising computer readable instructions, such that when executed by at least one processor, causes the processor to:

receive, by a streaming server operatively coupled with a first communication channel, a second communication channel, a cranial sensor system, and a remote device, cranial sensor output of a first data format, the first data format comprising raw data output comprising sensor response data generated by an ultrasonic sensor of the cranial sensor system, wherein the raw data output is associated with physiological measurements obtained by the ultrasonic sensor, and diagnostic output of a second data format different from the first data format, the diagnostic output comprising at least one of metadata, system state data of the cranial sensor system, control plane data associated with operation of the cranial sensor system, and diagnostic data derived from the cranial sensor output; and transmit, by the streaming server via the first communication channel from the cranial sensor system, to the remote device, the cranial sensor output, wherein the first communication channel is configured to losslessly transmit the cranial sensor output; and transmit, by the streaming server via the second communication channel from the cranial sensor system, to the remote device, the diagnostic output, wherein at least one of the first communication channel and the second communication channel is operable to transmit in a mirror mode corresponding to a first bandwidth, and wherein at least one of the first communication channel and the second communication channel is operable to transmit in an essential mode corresponding to a second bandwidth less than the first bandwidth.

16. The non-transitory computer-readable medium of claim 15, wherein the cranial sensor output comprises Transcranial Doppler ultrasound (TCD) output.

17. The non-transitory computer-readable medium of claim 15, wherein at least one of the first communication channel and the second communication channel transmits in real-time.

18. The non-transitory computer-readable medium of claim 15, wherein the second communication channel transmits losslessly.

19. The non-transitory computer-readable medium of claim 15, wherein the remote device comprises at least one of a smartphone, tablet, personal computer, computer, a television, a smart television, a smart watch, and a connected smart watch.

* * * * *